US005744317A

United States Patent [19]
Effros

[11] Patent Number: 5,744,317

[45] Date of Patent: Apr. 28, 1998

[54] DIAGNOSTIC TEST FOR REPLICATIVE SENESCENCE IN T CELLS

[75] Inventor: Rita B. Effros, Pacific Palisades, Calif.

[73] Assignee: The Reagents of the University of California, Oakland, Calif.

[21] Appl. No.: 755,291

[22] Filed: Nov. 22, 1996

Related U.S. Application Data

[63] Continuation of Ser. No. 307,508, Sep. 16, 1994, abandoned.

[51] Int. Cl.[6] ........................ G01N 33/53; G01N 33/555; G01N 33/567; C07K 16/00

[52] U.S. Cl. ............................ 435/7.24; 435/2; 435/810; 435/7.92; 435/974; 436/164; 436/172; 436/536; 436/811; 530/388.1; 530/341.3

[58] Field of Search .................................... 435/7.1, 7.24, 435/7.25, 7.94, 968, 2, 974; 436/518, 519, 538, 536, 63, 164, 172, 805, 811; 530/388.1, 388.15, 391.3; 422/73, 91, 92, 93

[56] References Cited

PUBLICATIONS

Experimental Gerontology, vol. 29, No. 6, issued 1994, Effros et al., "Decline in CD28+ T cells in centenarians and in long-term T cell cultures: A possible cause for both in vivo and in vitro immunosenescence", pp. 601–609 (see entire document).

Journal of Immunology, vol. 150, No. 4, Issued Feb. 15, 1993, Azuma et al, "CD28–T lymphocytes: Antigenic and functional properties", pp. 1147–1150, especially Figures 2B–C, 4B and 7A and p. 1153.

S. J. Wayne et al., "Cell-Mediated Immunity as a Predictor of Morbidity and Mortality in Subjects Over 60," *J. Gerontol.* 45:M45–48 (1990) (Exhibit 1).

M. L. Thoman & W.O. Weigle, "The Cellular and Subcellular Bases of Immunosenescence," *Adv. Immunol.* 46:221–261 (1989) (Exhibit 2).

I.C. Roberts-Thompson et al., "Ageing, Immune Response, and Mortality," *Lancet,* Aug. 17, 1974, pp. 368–370. (Exhibit 3).

G.R. Burgio & A.G. Ugazio, "Immunity in Down's Syndrome," *Eur. J. Pediatr.* 127:293–294 . (1978). (Exhibit 4).

(List continued on next page.)

*Primary Examiner*—Christopher L. Chin
*Assistant Examiner*—Bao-Thuy L. Nguyen
*Attorney, Agent, or Firm*—Morrison & Foerster LLP

[57] ABSTRACT

A method for distinguishing replicatively senescent T cells from replicatively non-senescent T cells in a cell population comprises the steps of: (1) providing a cell population of peripheral blood mononuclear cells; (2) reacting the cell population with a first monoclonal antibody specific for CD3 antigens which is present on all T cells, the antibody being labeled with a first detectable label, so that the monoclonal antibody binds to all T cells in the cell population; (3) simultaneously reacting the cell population with a second monoclonal antibody specific for CD28 antigen, the antibody being labeled with a second detectable label distinguishable from the first detectable label, so that the second monoclonal antibody binds to T cells positive for CD28; and (4) in the cell population of peripheral blood mononuclear cells, detecting the T cells that simultaneously react with the first monoclonal antibody and the second monoclonal antibody by observing the first detectable label bound to the cells simultaneously with the second detectable label bound to the cells, thereby distinguishing replicatively senescent T cells, which are CD28-negative, from replicatively non-senescent T cells, which are CD28-positive, and determining any of: (a) the number of replicatively senescent T cells in the cell population; (b) the number of replicatively non-senescent T cells in the cell population; or (c) the proportion of replicatively senescent T cells to replicatively non-senescent T cells in the cell population. The method can also be used to separate and isolate cells showing immunological senescence from non-senescent cells.

13 Claims, 3 Drawing Sheets

% CD28 + CELLS
100
80
60
40
20
0
CONTROL
AGED

PUBLICATIONS

S.R.S. Rangan & P. Armatis, "Enhanced Frequency of Spontaneous B Cell Lines from Epstein–Barr Virus (EBV) Seropositive Donors 80 Years and Older," *Exp. Gerontol.* 26:541–547 (1991) (Exhibit 5).

L. Hayflick, "The Limited In Vitro Lifetime of Human Diploid Cell Strains," *Exp. Cell Res.* 37:614–636 (1965) (Exhibit 6).

T. H. Norwood & J.R. Smith, "The Cultured Fibroblast–Like Cell as a Model for the Study of Aging," *in Handbook of the Biology of Aging* (C.E. Finch & E.L. Schneider, eds., Van Nostrand Reinhold, New York, 1985), ch. 12, pp. 291–320 (Exhibit 7).

N.L. Perillo et al., "Human T. Lymphocytes Possess a Limited In Vitro Lifespan," *Exp. Gerontol.* 24:177–187 (1989) (Exhibit 8).

C.H. June et al., "T–Cell Proliferation Involving the CD28 Pathway as Associated With Cyclosporine–Resistant Interleukin 2 Gene Expression," *Mol. Cell. Biol.* 7:4472–4481 (1987) (Exhibit 9).

M. Azuma et al., "CD28– T Lymphocytes: Antigenic and Functional Properties," *J. Immunol.* 150:1147–1159 (1993) (Exhibit 10).

C.L. Verweij et al., "Activation of Interleukin–2 Gene Transcription via the T–Cell Surface Molecule CD28 Is Mediated Through an NF–kB–Like Response Element," *J. Biol. Chem.* 266:14179–14182 (1991) (Exhibit 11).

M.K. Jenkins, et al., "CD28 Delivers a Costimulatory Signal Involved in Antigen–Specific IL–2 Production by Human T Cells," *J. Immunol.* 147:2461–2466 (1991) (Exhibit 12).

S.E. Townsend & J.P. Allison, "Tumor Rejection After Direct Costimulation of cD8+ T–Cells by B7–Transfected Melanoma Cells," *Science* 259:368–370 (1993) (Exhibit 13).

P. Tan et al., "Induction of Alloantigen–Specific Hyporesponsiveness in Human T Lymphocytes by Blocking Interaction of CD28 with Its Natural Ligand B7/BB1," *J. Exp. Med.* 177:165–173 (1993) (Exhibit 14).

N.L. Perillo et al., "The In Vitro Senescence of Human T Lymphocytes: Failure to Divide Is Not Associated with a Loss of Cytolytic Activity or Memory T Cell Phenotype," *Mech. Ageing & Develop.* 67: 174–185 (1993) (Exhibit 15).

D. R. DeSilva et al., "Clonal Anergy Is Induced In Vitro by T Cell Receptor Occupancy in the Absence of Proliferation," *J. Immunol.* 147:3261–367 (1991) (Exhibit 16).

Y. Liu & C.A. Janeway, Jr., "Interferon γ Plays a Critical Role in Induced Cell Death of Effector T Cell: A Possible Third Mechanism of Self–Tolerance," *J. Exp. Med.* 172:1735–1739 (1990) (Exhibit 17).

A. Grosman et al., "Reduced Proliferation in T Lymphocytes in Aged Humans Is Predominantly in the CD8+ Subset, and is Unrelated to Defects in Transmembrane Signaling Which are Predominantly in the CD4+ Subset," *Exp. Cell Res.* 180:367–382 (1989) (Exhibit 18).

R.A. Miller, "Age–Associated Decline in Precursor Frequency for Different T Cell–Mediated Reactions, with Preservation of Helper or Cytotoxic Effect per Precursor Cell," *J. Immunol.* 132:63–68 (1984) (Exhibit 19).

C.A. Michie et al., "Lifespan of Human Lymphocyte Subsets Defined by CD45 Isoforms," *Nature* 360:264–268 (1992) (Exhibit 20).

A. Shahinian et al., "Differential T Cell Costimulatory Requirements in CD28–Deficient Mice," *Science* 261:609–612 (1993) (Exhibit 21).

M. Azuma et al., "Requirements for CD28–Dependent T Cell–Mediated Cytotoxicity," *J. Immunol* 150:2091–2101 (1993) (Exhibit 22).

R.A. Miller, "Aging and the Immune Response," *In Handbook of the Biology of Aging* (3d ed., E.L. Schneider & J.W. Rowe, eds., Academic Press, Inc., San Diego, 1990), Ch. 9, pp. 157–180. (Exhibit 23).

R.B. Effros, "Immunosenescence–Related Diseases in the Elderly," *Immunol. & Allergy Clin. North Am.* 13:695–712 (1993) (Exhibit 24).

June et al., Immunol. Today, 11(6):211–216, 1990.

Kozbov et al., J. Immunol, 138(12):4128–4132, 1987.

Clark et al., Eur. J. Immunol., 17: 1799–1805, 1987.

AMAC Catalog of Antibodies and Immunoassays (1992) pp. 13–15.

Morishita et al., J. Immunol., 136(6):2095–2102, 1986.

Damle et al., J. Immunol., 132(2):644–650, 1984.

Lum et al., Cell. Immunol., 72: 122–129, 1982.

DIAGNOSTIC TEST FOR REPLICATIVE SENESCENCE IN T CELLS

This application is a continuation of application Ser. No. 08/307,508, filed 16 Sep. 1994, now abandoned.

GOVERNMENT RIGHTS

This invention was supported by grants from the United States government, namely Grant Nos. AG05309, AG00427, and AG00424, from the National Institutes of Health. Accordingly, the government may have certain rights in this invention.

BACKGROUND OF THE INVENTION

This invention is directed to a diagnostic test for certain types of immune deficiency, particularly in the elderly.

There is a vast literature documenting clinical and pathological evidence of diseases common in the elderly population. Some of these conditions can be directly traced to specific immune deficits, whereas others are clearly independent of immune senescence. Between these two extremes is a "grey area" which represents diseases or conditions showing varying degrees of immunological involvement, some of which may not be immediately evident. As originally predicted by Roy Walford in his "Immunological Theory of Aging" (R. L. Walford, "Immunologic Theory of Aging" (Munksgaard, Copenhagen, 1969)), age-related changes in immune function could contribute to a wide range of degenerative diseases not ordinarily considered immunologic in etiology. Thus, uncovering some of the more subtle immunological relationships is an important aspect of the endeavor to develop suitable prophylactic or therapeutic approaches for the elderly.

In particular, aging is accompanied by a dramatic decline in immune functions involving both B and T cells (M. L. Thoman & W. O. Weigle, "The Cellular Bases of immunosenescence," *Adv. Immunol.* 46:221–261 (1989); R. A. Miller, "Aging and the immune Response," in *Handbook of the Biology of Aging* (E. L. Schneider & J. W. Rowe, eds., 3d ed., Academic Press, Inc., 1990), ch. 9, pp. 157–180)).

The importance of exploring the putative relationships between specific immunological deficits and certain diseases of aging which result from or at least are contributed to by these deficits, is highlighted by three provocative sets of findings: S. Wayne et al., "Cell-Mediated Immunity as Predictor of Morbidity and Mortality in Subjects Over 60, " *Exp. Gerontol.* 45:M45 (1990), J. C. Roberts-Thompson et al., "Aging, Immune Response and Mortality," *Lancet* 2:368 (1974), and D. M. Murasko et al., "Association of Lack of Mitogen Induced Lymphocyte Proliferation with Increased Mortality in the Elderly," *Aging: Immunol. & Infect. Dis.* 1:1 (1988). These investigators reported, in prospective studies of elderly subjects, that low responsiveness, both in DTH tests for common recall antigens and in T cell mitogen stimulation tests, was predictive of mortality over the subsequent few years. The latter two studies noted that the most common cause of death were sudden death, cardiovascular disease, and infections. Furthermore, D. M. Murasko et al. (1988), supra, reported that the immune function tests retained their prognostic value even when subjects with neoplastic disease or undergoing immunosuppressive therapy were eliminated. Thus, immunological assays can potentially be used as biomarkers to identify the subpopulation of aged individuals who are at greatest risk, and their predictive value is maintained even when mortality is due to conditions not usually considered primarily as "immunological".

The greater risk of elderly populations includes infectious diseases, both bacterial and vital. Examples of infectious diseases that are more severe in the elderly are tuberculosis and influenza. Down's syndrome is considered a model of accelerated aging in humans, and individuals with Down's syndrome have a greatly increased risk of death from infectious diseases, particularly respiratory infections (J. Oster et al., in *Proceedings of the international Copenhagen Congress Scientific Study of Mental Retardation* (1964), vol. 1, p. 231). In addition, these patients have a greatly increased prevalence of hepatitis B surface antigen, possibly because of diminished capacity for viral clearance (G. R. Burgio & A. G. Ugazio, "Immunity in Down's Syndrome," *Eur. J. Pediatr.* 127:293 (1978)).

Another aspect of immunological decline may be exacerbation of the course of acquired immune deficiency syndrome (AIDS) in the elderly (S. Ferro & J. E. Salit, "HIV Infection in Patients over 55 Years of Age," *J. AIDS* 5:348 (1992)).

Still another aspect of immunological decline in the elderly is likely to be an increase in the occurrence of malignancies, although the development of malignancies is a complex multifactorial process. An example of the processes that may lead to increased occurrence of malignancies in the immunocompromised elderly is provided by the behavior of Epstein-Barr virus (EBV). It is well known that infectious mononucleosis, an acute infectious disease caused by EBV, is often more severe in adults than in children, and the persistence of EBV may lead to malignancy. It has been demonstrated that there is a significantly increased occurrence of spontaneous EBV-transformed lymphoblastoid cell lines from healthy donors over age 79 as compared with younger donors (S. R. S. Rangan & P. Armatis, "Enhanced Frequency of Spontaneous B Cell Lines from Epstein-Barr Virus (EBV) Seropositive Donors 80 Years and Older," *Exp. Gerontol.* 26:541 (1991)).

Many other diseases and conditions that are more common in the elderly may have some immune component. These include atherosclerosis, diabetes, Alzheimer's Disease, and lung diseases (R. B. Effros, "Immunosenescence-Related Diseases in the Elderly," *Immunol. & Allerg. Clinics of North America* 13:695–712 (1993)).

Still another example of an immunologically-based medical problem of the elderly is a diminished antibody responses to specific vaccines (R. B. Effros (1993), supra.

A consensus has emerged that changes in the relative proportions of T and B lymphocytes or in distribution of T cells between the CD4 and CD8 sets, while occasionally demonstrable in specific clinical populations or animal colonies, are unlikely to explain age-related declines in immune function. (R. A. Miller (1990), supra).

However, despite a large body of research on the nature of these immunological deficits, there is no known mechanism which explains the progressive decline of immune competence with age. Nor is there a reliable biomarker to identify which subset of chronologically old individuals are at risk immunologically.

Therefore, there exists a need for an improved method of determining immune senescence. Such an improved method should be broadly applicable and should not be dependent on markers or antigens that are found in only small subpopulations of immune-competent cells or whose occurrence varies markedly from individual to individual. Such a method should also be relatively easy to carry out and interpret, while yielding results of predictive value, both for mortality and morbidity in general, and for susceptibility to particular immune-related conditions. Such a method should also be capable of combination with other screening methods for other markers so that a number of parameters of the cells can be determined in parallel.

SUMMARY

An improved method for determining immune senescence is based on the discovery that T cells lacking CD28 antigen are inhibited in proliferation to stimuli such as restimulation with antigen, exposure to anti-CD3 antibody in combination with anti-CD28 antibody, or exposure to increasing doses of IL-2. Thus, detecting $CD28^+$ T cells and separating them from $CD28^-$ T cells provides a method of determining immune senescence.

One aspect of the present invention is a method for distinguishing replicatively senescent T cells from replicatively non-senescent T cells in a cell population of peripheral blood mononuclear cells. This method comprises the steps of:

(1) providing a cell population of peripheral blood mononuclear cells;

(2) reacting the cell population with a first monoclonal antibody specific for CD3 antigen, which is present on all T cells, the antibody being labeled with a first detectable label, so that the monoclonal antibody binds to all T cells in the cell population;

(3) simultaneously reacting the cell population with a second monoclonal antibody specific for CD28 antigen, the antibody being labeled with a second detectable label distinguishable from the first detectable label, so that the second monoclonal antibody binds to T cells positive for CD28; and (4) in the cell population of peripheral blood mononuclear cells, detecting the T cells that simultaneously react with the first monoclonal antibody and the second monoclonal antibody by observing the first detectable label bound to the cells simultaneously with the second detectable label bound to the cells, thereby distinguishing replicatively senescent T cells, which are CD28-negative, from replicatively non-senescent T cells, which are CD28-positive, and determining any of: (a) the number of replicatively senescent T cells in the cell population; (b) the number of replicatively non-senescent T cells in the cell population; or (c) the proportion of replicatively senescent T cells to replicatively non-senescent T cells in the cell population.

Typically, the detectable label is a fluorescent label. Typically, the step of detecting the cells that react with the monoclonal antibody by observing the detectable label bound to the cells is performed using fluorescence activated cell sorting (FACS). The cell population is from peripheral blood.

The cell population can population of lymphocytes obtained from a patient.

Typically, the first and second detectable labels are fluorescent labels and the CD3-positive cells and the CD28-positive cells, are detected by fluorescence-activated cell sorting (FACS). Typically, the FACS is performed in one step to yield a two-dimensional plot.

This method can further comprise the steps of:

(5) reacting the CD3-positive cells that are either immunologically non-senescent (CD28-positive) or immunologically senescent (CD28-negative) with at least one other monoclonal antibody selected from the group consisting of an anti-CD4 monoclonal antibody and an anti-CD8 monoclonal antibody labeled with a detectable label; and (6) determining the proportion of the CD3-positive cells that are either immunologically non-senescent or immunologically senescent that binds to the at least one other monoclonal antibody by observing the detectable label bound to the cells.

Another aspect of the present invention is a method for separating immunologically senescent cells from immunologically non-senescent cells in a cell population. This method comprises the steps of:

(1) providing a cell population of peripheral blood mononuclear cells;

(2) reacting the cell population with a first monoclonal antibody specific for CD3 antigen, which is present on all T cells, the antibody being labeled with a first detectable label, so that the monoclonal antibody binds to all T cells in the cell population;

(3) simultaneously reacting the cell population with a second monoclonal antibody specific for CD28 antigen, the antibody being labeled with a second detectable label distinguishable from the first detectable label, so that the second monoclonal antibody binds to T cells positive for CD28 to define a first subpopulation of CD28-positive, replicatively non-senescent T cells and a second subpopulation of CD28-negative, replicatively senescent T cells; and (4) separating the first subpopulation of T cells from the second subpopulation of T cells by fluorescent activated cell sorting (FACS) to produce a separated first subpopulation of relicatively non-senescent T cells and a separated second subpopulation of replicatively senescent T cells.

Another aspect of the present invention is the first and second subpopulations produced by this method.

Yet another aspect of the present invention is a kit for distinguishing immunologically senescent cells from immunologically non-senescent cells in a cell population, comprising, in separate containers:

(1) an anti-CD3 monoclonal antibody labeled with a first detectable label; and (2) an anti-CD28 monoclonal antibody labeled with a second detectable label.

The kit can further comprise, in an additional separate container:

(3) at least one other monoclonal antibody selected from the group consisting of an anti-CD4 monoclonal antibody and an anti-CD8 monoclonal antibody labeled with a detectable label.

BRIEF DESCRIPTION OF THE DRAWINGS

These and other features, aspects, and advantages of the present invention will become better understood with reference to the following description, appended claims, and accompanying drawings where:

DESCRIPTION

Figure 1A:
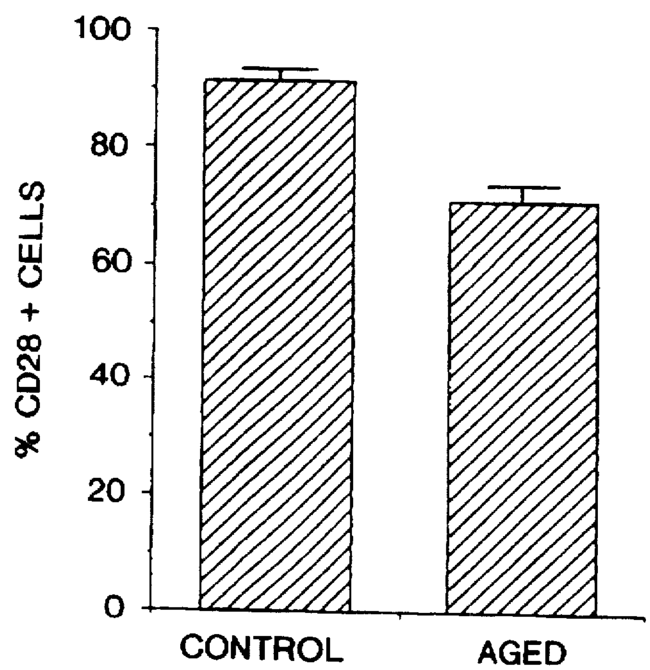
FIGS. 1A and 1B shows the expression of CD28 on peripheral blood T cells of centenarians and controls. Flow cytometric analysis was performed on 20,000 cells per sample ((A) Mean (+S.E.M.) percent $CD28^+$ for control and centenarian cohorts. (% $CD28^+$=$CD28^+$ cells-isotype control/total $CD3^+$ cells-isotype control); (B) proportion of CD28-positive T cells for individual donors).

In an effort to analyze the basic mechanisms involved in T cell proliferative decline with age, I have developed a culture system to study the growth control of T lymphocytes in a fashion analogous to that of the well-established model of fibroblast cellular senescence (L. Hayflick, "The Limited in Vitro Lifetime of Human Diploid Cell Strains," *Exp. Cell Res.* 180:367–382 (1965); T. H. Norwood & J. R. Smith, "The Cultured Fibroblast-Like Cell as a Model for the Study of Aging" in *Handbook of the Biology of Aging* (C. E. Finch & E. L. Schneider, eds., Van Nostrand Reinhold Co., New York, 1985), pp. 291–321. The results with this culture system show that, like fibroblasts, normal human T lymphocytes have a limited proliferative potential (Perillo et al. 1989). The senescent T cells nevertheless function normally in antigen recognition and cytotoxicity (N. L. Perillo et al., "Human T Lymphocytes Possess a Limited in Vitro Lifespan," *Exp. Gerontol.* 24:177–187 (1989)). Since certain T cell costimulatory events are essential for activation leading to proliferation (C. H. June et al., "T-Cell Interleukin 2 Gene Expression," *Molec. Cell Biol.* 7:4472–4481 (1987)), but are not necessarily required for cytotoxic function itself (A. Azuma et al., "CD28- T Lymphocytes: Antigenic and Functional Properties," *J. Immunol.* 150:1147–1159 (1993)), the possible involvement of one such molecule, CD28, in T cell senescence, was investigated.

The CD28 glycoprotein, expressed on the surface of most mature T cells, is currently the focus of intensive investigation due to its critical role in costimulatory events that occur along with engagement of the T-cell antigen receptor (TCR). Recent reports have shown that CD28 signaling: (a) operates through a pathway distinct from that of the TCR, (b) is insensitive to Cyclosporin A, and (c) functions in the activation of IL-2 gene transcription by induction of the NF-κB-like response element and also by stabilization of the lymphokine mRNA (C. H. June et al. (1987), supra; C. L. Verweij et al., "Activation of Interleukin-2 Gene Transcription via the T-Cell Surface Molecule CD28 Is Mediated Through an NF-κB-Like Response Element," *J. Biol. Chem.* 266:14179–14182 (1991); M. K. Jenkins et al., "CD28 Delivers a Costimulatory Signal Involved in Antigen-Specific IL-2 Production by Human T Cells," *J. Immunol.* 147:2461–2466 (1991)).

Several experimental observations suggest that CD28 signal transduction may be a crucial determinant of the outcome of TCR stimulation. For example, the experimentally-induced T-cell mediated rejection of a transplantable melanoma in mice is entirely dependent on the presence of the CD28 ligand on the tumor cells (S. E. Townsend & J. P. Allison, "Tumor Rejection After Direct Costimulation of CD28+ T Cells by B7-Transfected Melanoma Cells," *Science* 259: 368–370 (1993)). Conversely, the absence of CD28 engagement following antigenic stimulation of T-cell clones results in a state of long-term antigen-specific hyporesponsiveness (P. Tan et al., "Induction of Alloantigen-Specific Hyporesponsiveness in Human T Lymphocytes by Blocking Interaction of CD28 with Its Natural Ligand B7/BB1," J. Exp. Med. 177:165–173 (1993)).

In light of the newly defined critical nature of costimulatory events in the optimal activation of T lymphocytes, the present study was designed to test the hypothesis that T cell senescence, both in vivo and in vitro, is correlated with a decline in the percentage of T-cells bearing the CD28 molecule, and, therefore, that immune senescence might reflect a Hayflick phenomenon operating in vivo. Thus, the original concept derived from work with cultured cells that had reached replicative senescence. However, no cell culturing is required to practice the method of the present invention.

The term "immune senescence," as used herein, refers to cells of the immune system, particularly T cells, that are incapable of proliferating. In particular, proliferation is not observed in immune senescent cells following restimulation with antigen, exposure to anti-CD3 antibody in combination with anti-CD28 antibody, or exposure to increasing doses of IL-2. These cells may show no other functional deficits. However, cells that do show additional functional deficits but are incapable of proliferating are still within the definition of immune senescence.

One aspect of the present invention is a method for distinguishing immunologically senescent cells from immunologically non-senescent cells in a cell population. In general, this method comprises the steps of:

(1) providing a cell population of peripheral blood mononuclear cells;

(2) reacting the cell population with a first monoclonal antibody specific for CD3 antigen, which is present on all T cells, the antibody being labeled with a first detectable label, so that the monoclonal antibody binds to all T cells in the cell population;

(3) simultaneously reacting the cell population with a second monoclonal antibody specific for CD28 antigen, the antibody being labeled with a second detectable label distinguishable from the first detectable label, so that the second monoclonal antibody binds to T cells positive for CD28; and (4) in the cell population of peripheral blood mononuclear cells, detecting the T cells that simultaneously react with the first monoclonal antibody and the second monoclonal antibody by observing the first detectable label bound to the cells simultaneously with the second detectable label bound to the cells, thereby distinguishing replicatively senescent T cells, which are CD28-negative, from replicatively non-senescent T cells, which are CD28-positive, and determining any of: (a) the number of replicatively senescent T cells in the cell population; (b) the number of replicatively non-senescent T cells in the cell population; or (c) the proportion of replicatively senescent T cells to replicatively non-senescent T cells in the cell population.

Monoclonal antibodies to CD28 antigen are well-known in the art and need not be described further herein. A particularly suitable anti-CD28 monoclonal antibody is produced and distributed by The Central Laboratory for Blood Transfusion, Amsterdam, Netherlands, and is conjugated to the fluorescent label fluorescein isothiocyanate. Other anti-CD28 monoclonal antibodies are known in the art and can be used as long as they bind to the same epitope of the CD28 antigen by cross-competition assays.

Methods for binding these monoclonal antibodies to cells are also well known and need not be described further. Typically, these methods involve binding the antibodies to the cell surface in a buffered saline solution that is isotonic or nearly isotonic. The buffered saline solution can also have a carrier protein such as bovine serum albumin.

As indicated, typically, the detectable label is a fluorescent label such as fluorescein isothiocyanate, phycoerythrin, rhodamine isothiocyanate, or Texas Red. These labels are typically covalently conjugated to monoclonal antibodies, and methods for such conjugation are described in, for example, E. Harlow & D. Lane, "Antibodies: A Laboratory Manual" (Cold Spring Harbor Laboratory Press, Cold Spring Harbor, N.Y., 1988), pp. 353–358. Other conjugation methods are also well-known in the art.

Although fluorescent labels are generally preferred, other labels, such as radioactive labels, chemiluminescent labels, or bioluminescent labels, can be used. Still other labels are well known in the art and can be used as alternatives.

The step of detecting the cells that react with the monoclonal antibody by observing the detectable label bound to the cells is typically performed using fluorescence activated cell sorting (FACS), also known as flow cytometry. FACS machines are commercially available and their use need not be described further here. FACS is further described in, e.g., J. W. Goding, "Monoclonal Antibodies: Principles and Practice" (2d ed., Academic Press, London, 1986), pp. 252–255. FACS can be used for either cell preparation or cell analysis. As described below, two-dimensional analysis and separation can be performed, sorting cells into, e.g., 4 (2×2) groups.

The cell population can be a population of lymphocytes obtained from a patient; similar diagnostic conclusions can be drawn from the number and/or ratio of cell populations obtained by the analysis described above.

Suitable anti-CD3 antibodies are also well-known in the art. One particularly suitable anti-CD3 antibody is phycoerythrin-conjugated anti-CD3 monoclonal antibody, obtainable from Caltag, South San Francisco, Calif. Other anti-CD3 monoclonal antibodies are known in the art. As with anti-CD28 antibody, other anti-CD3 antibodies can be used as long as they bind to the same epitope of the CD3 antigen by cross-competition assays.

Typically, in this method, the first and second detectable labels are fluorescent labels. The subpopulation of cells positive for CD3 antigen, as well as the cells bound to the first antibody, are detected by fluorescence-activated cell sorting (FACS). The FACS is typically performed in one step to yield a two-dimensional plot.

This method can also further comprise:

(5) reacting the CD3-positive cells that are either immunologically non-senescent (CD28-positive) or immunologically senescent (CD28-negative) with at least one other monoclonal antibody selected from the group consisting of an anti-CD4 monoclonal antibody and an anti-CD8 monoclonal antibody labeled with a detectable label; and (6) determining the proportion of the CD3-positive cells that are either immunologically non-senescent or immunologically senescent that binds to at least one other monoclonal antibody by observing the detectable label bound to the cells.

These antibodies are used to distinguish helper T cells from cytotoxic T cells. Typically, helper T cells are $CD4^+$, while cytotoxic T cells are $CD8^+$. Suitable monoclonal antibodies for these antigens are well-known in the art. Examples are phycoerythrin-conjugated anti-CD4 monoclonal antibodies and fluorescein isothiocyanate-conjugated anti-CD8 monoclonal antibodies, both available from Caltag, South San Francisco, Calif. Other antibodies are known in the art and can be used.

Another aspect of the invention is a method for separating replicatively non-senescent T cells from replicatively non-senescent T cells in a cell population. This method makes use of the preparative capacities of the FACS machine. In general, this method comprises the steps of:

(1) providing a cell population of peripheral blood mononuclear cells;

(2) reacting the cell population with a first monoclonal antibody specific for CD3 antigen, which is present on all T cells, the antibody being labeled with a first detectable label, so that the monoclonal antibody binds to all T cells in the cell population;

(3) simultaneously reacting the cell population with a second monoclonal antibody specific for CD28 antigen, the antibody being labeled with a second detectable label distinguishable from the first detectable label, so that the second monoclonal antibody binds to T cells positive for CD28 to define a first subpopulation of CD28-positive, replicatively non-senescent T cells and a second subpopulation of CD28-negative, replicatively senescent T cells; and (4) separating the first subpopulation of T cells from the second subpopulation of T cells by fluorescent activated cell sorting (FACS) to produce a separated first subpopulation of replicatively non-senescent T cells and a separated second subpopulation of replicatively senescent T cells.

Another aspect of the present invention is the populations of sorted cells produced by this method. These populations include a first subpopulation of immunologically non-senescent cells, and a second subpopulation of immunologically senescent cells. These subpopulations can be isolated by separating the cells into individual fluid droplets that can be electrostatically deflected into tubes.

Still another aspect of the present invention is a kit for distinguishing immunologically senescent cells from immunologically non-senescent cells in a cell population. This kit, comprises, in separate containers:

(1) an anti-CD3 monoclonal antibody labeled with a first detectable label; and (2) an anti-CD28 monoclonal antibody labeled with a second detectable label.

The kit can further comprise, in an additional separate container:

(3) at least one other monoclonal antibody selected from the group consisting of an anti-CD4 monoclonal antibody and an anti-CD8 monoclonal antibody labeled with a detectable label.

The present invention is illustrated by the following Example. The Example is for illustrative purposes only and is not intended to limit the invention.

EXAMPLE

Decline of CD28-Positive Cells in Centenarians and in Long-Term T-Cell Cultures The original concept of the invention, as exemplified in this Example, derived from work with cultured cells that had reached replicative senescence. However, no cell culturing is required to practice the method exemplified in this Example.

Methods and Materials

Sources of T lymphocytes.

Peripheral blood samples were obtained from 21 healthy centenarians (CEPH) and 20 healthy controls ranging in age from 25–69. The controls consisted of 10 subjects from a UCLA donor cohort and 10 from the CEPH donor cohort. (The mean values for % CD28+ T cells from these two groups did not differ significantly despite the fact that all the controls age 50 or more happened to be in the UCLA group.) The UCLA and CEPH control donors were "healthy" according to UCLA and Hopital St. Louis Blood Bank criteria respectively, and the centenarians all responded to advertisements for "healthy donors needed for aging study". This study conformed to the UCLA and CEPH Human Use Committee guidelines, and all subjects gave written and informed consent. Mononuclear cells were separated by Ficoll-Hypaque density centrifugation and cryopreserved in liquid nitrogen. In preparation for antibody staining, samples were thawed rapidly at 37° C., washed once in RPMI containing 20% fetal bovine serum, and twice in Hanks Balanced Salt Solution (HBSS).

Cell cultures.

T cell cultures were initiated as previously described (N. L. Perillo et al. (1989), supra). Briefly, $10^6$ mononuclear cells were mixed with $10^6$ irradiated (8,000 Rad) allogeneic EBV-transformed B cells. After the initial ten day activation period, cultures were maintained in AIM V™ serum-free medium (Gibco, Gaithersburg, Md., U.S.A.) containing 25 Units/ml recombinant IL-2 (Amgen, Thousand Oaks, Calif., U.S.A.), and were subcultivated to a density of $2\times10^5$/ml whenever the cell counts exceeded $8\times10^5$/ml. Restimulation was performed every 3–4 weeks using the same lymphoblastoid cells as in the original activation culture. At each passage, viable cell counts (determined by trypan blue dye exclusion) were recorded and used to calculate the number of population doublings since the previous passage. The 100% value for "% proliferative lifespan completed" is equivalent to the cumulative number of population doublings completed Flow cytometry.

The following antibodies were used for staining: fluorescein-isothiocyanate (FITC)-conjugated mAb to CD28 (Central Laboratory for Blood Transfusion, Amsterdam, Netherlands), phycoerythrin (PE)-conjugated mAb to CD3, PE-conjugated mAb to CD4, FITC-conjugated mAb to CD8, isotype controls IgG2a-PE,IgGl-FITC (all from Caltag, South San Francisco, Calif., USA). Some of the samples from the control group were stained with mAb to CD3-FITC and mAb to CD28-PE (Becton-Dickinson, San Jose, Calif. USA), with results essentially identical to the CD3-PE and CD28-FITC staining. All of the centenarian samples and 10 of the control samples were doubly stained with CD28 and CD3 and were analyzed in two-color histograms. Aliquots of $10^6$ cells were washed twice in staining buffer (PBS or HBSS containing 1% BSA) then resuspended in the appropriate concentration of monoclonal antibodies diluted in staining buffer. Samples were incubated for 45 minutes at 4° C. in the absence of light. Following two washes, cells were resuspended in buffered saline containing 1% paraformaldehyde. Flow cytometric analysis was performed on 20,000 cells per sample using a Coulter Elite flow cytometer.

Results

Expression of CD28 in vivo.

Figure 1B:
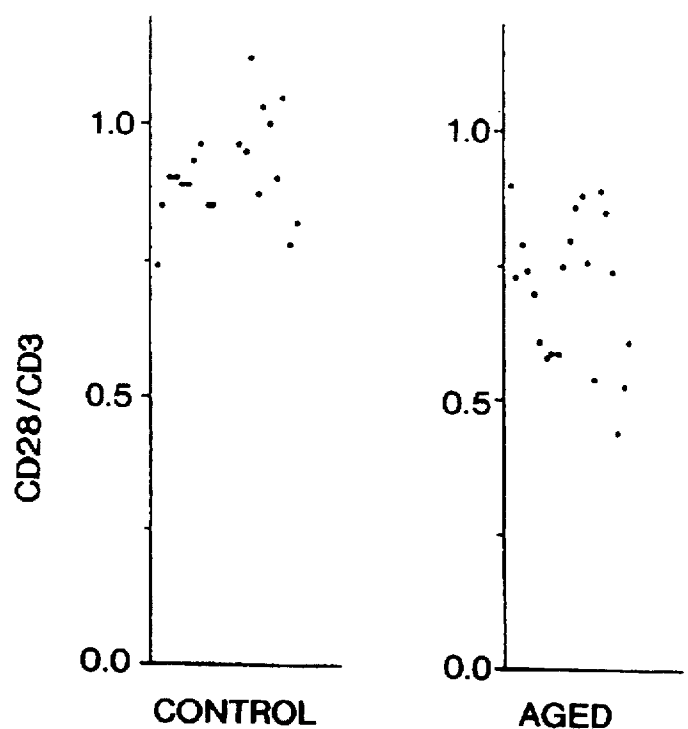
Figure 2B:
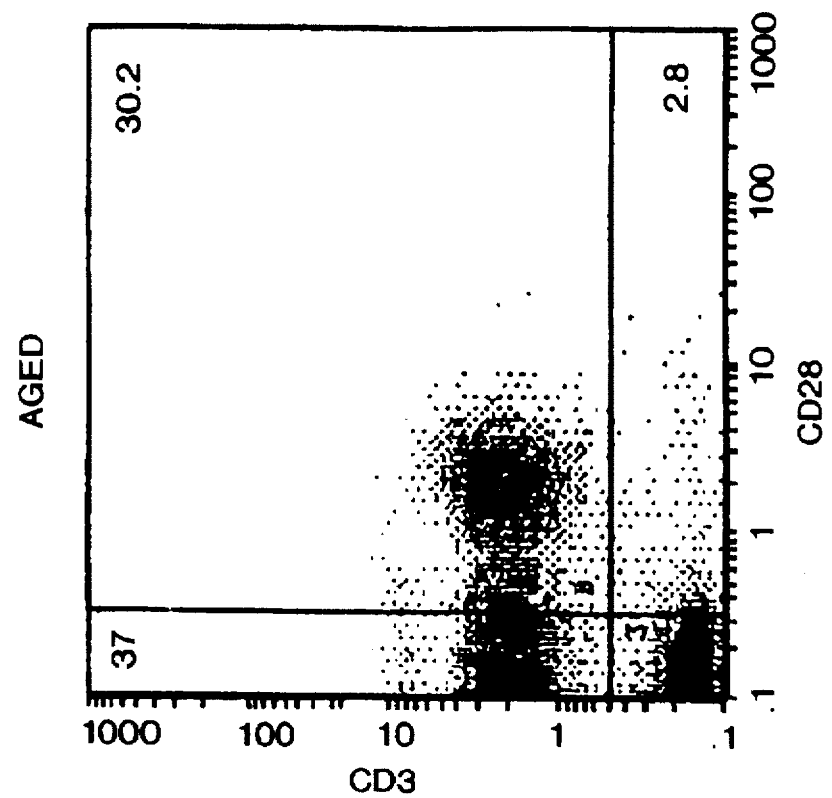
FIG. 2 shows the expression of CD28 and CD3 on centenarian and control peripheral blood mononuclear cells by flow cytometric analysis of samples from centenarian and control donors. Each sample was doubly-stained with the two monoclonal antibodies as described in the Example; the numbers in each quadrant indicate the percentages of cells scored as positive.
Figure 2A:
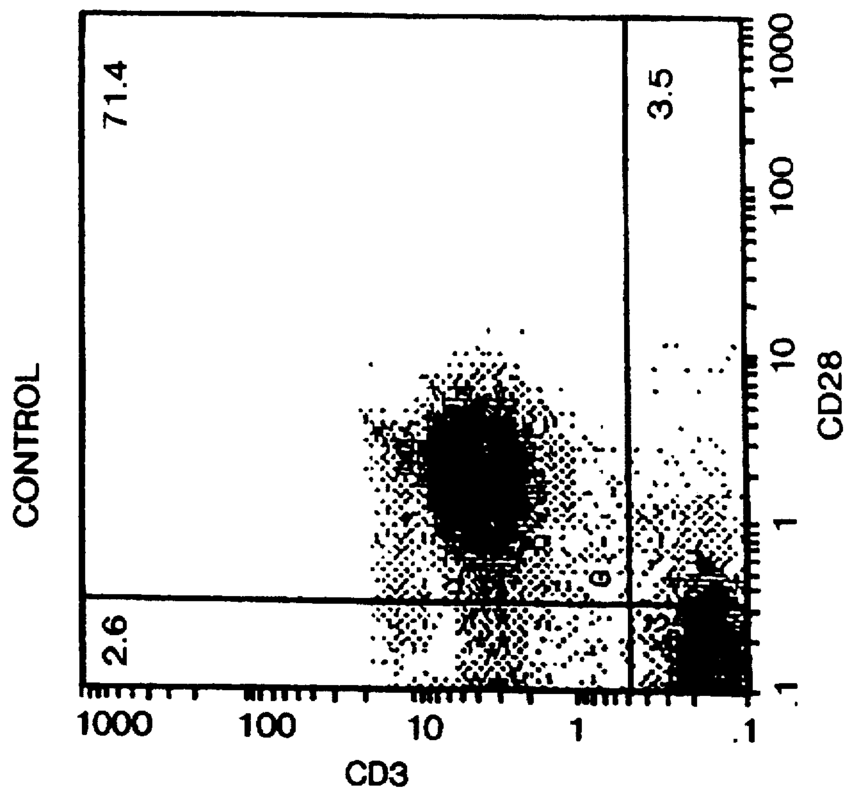

The percentages of $CD28^+$ cells in the peripheral blood T cells of 20 control and 21 centenarians were compared by flow cytometry. The data in FIG. 1A demonstrate a significant decrease ($p<0.001$) in the percentage of $CD28^+$ T-cells in the centenarian cohort. As shown in FIG. 1B, several of the aged individuals demonstrate values as low as 44, 53, and 54% in the percentage of $CD28^+$ T cells, compared to the mean control value of 91% $CD28^+$ cells. The FACS scatter plot shown in FIG. 2 is representative of the data obtained for the two cohorts. The decrease in the percentage of $CD28^+$ cells with age is not associated with an alteration in the intensity or standard deviation of mean fluorescence (data not shown), suggesting that the expression of CD28 is normal on those cells which do score as $CD28^+$.

T cell subset ratio.

Figure 3:
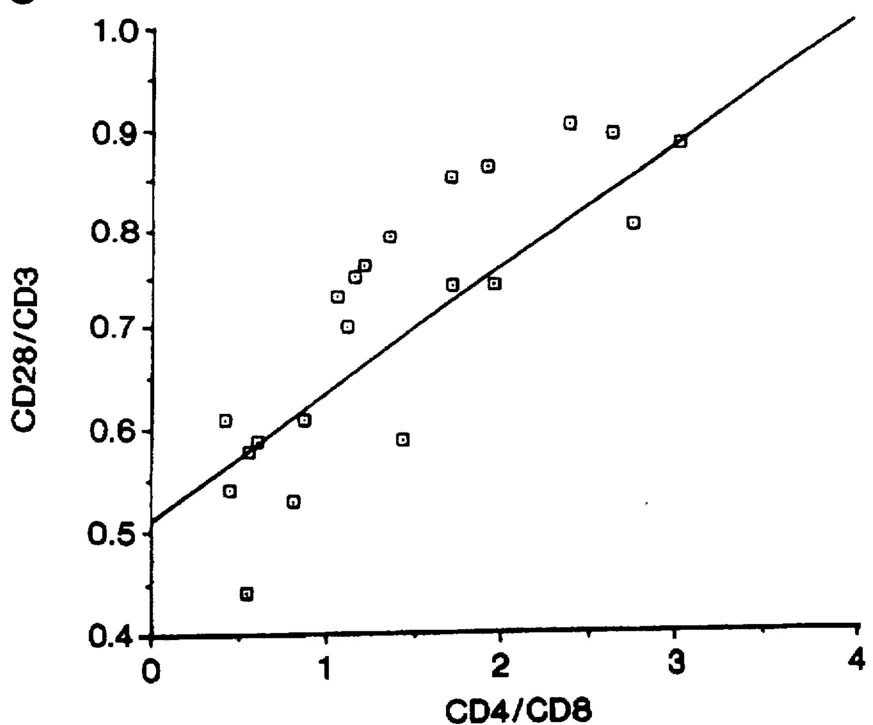
FIG. 3 shows the correlation between the percentage of $CD28^+$ cells and CD4/CD8 ratio in centenarians ($r^2$=0.695, p<0.0001).

Conflicting reports exist in the literature on whether aging is associated with shifts in the subsets of T cells (M. L. Thoman & W. O. Weigle (1989), supra). The CD4/CD8 ratios in the centenarian cohort was analyzed and, indeed, there was great variability in the values obtained, with a range of 0.45 to 2.38. However, as shown in FIG. 3, there is a significant correlation ($r^2=0.695$, $p<0.0001$) between the percentage of $CD28^+$ T-cells and the CD4/CD8 ratio.

Expression of CD28 in long-term T cell cultures.

In an effort to begin to define the mechanism involved in the loss of CD28 on a segment of the T cells in the centenarian cohort, the T cell culture system recently developed to examine cellular senescence in vitro was used. Using this model, it was shown that peripheral blood T cells of healthy adults activated repeatedly in vitro by allostimulation and cultured in the continuous presence of IL-2, undergo a finite number of population doublings (23±7) before reaching a state of proliferative senescence (N. L. Perillo et al. (1989), supra).

Figure 4:
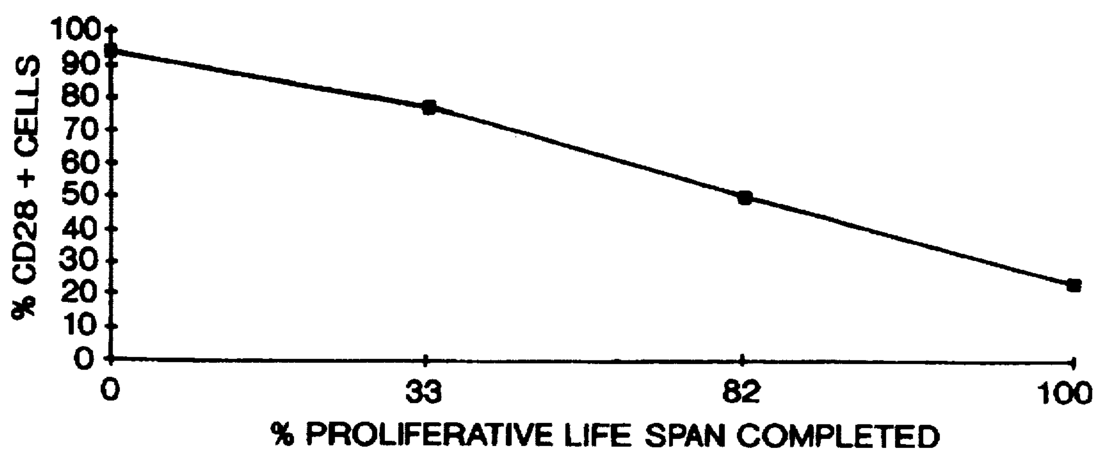
FIG. 4 shows the decline in $CD28^+$ T cells with in vitro cellular senescence. Flow cytometric analysis was performed on cultured T cells initiated from a normal adult donor. The 100% value for "% proliferative lifespan completed" is equivalent to the cumulative number of population doublings completed before senescence. All senescent cultures are >99% $CD3^+$. This figure is representative of the decline in CD28 expression observed in 4 separate experiments in which cultures derived from 4 individual donors were analyzed.

The senescent cultures, which are predominantly of the CDS+ T subset, are nevertheless viable, long-lived, and fully competent to recognize and lyse the specific allogeneic target to which they were sensitized (N. L. Perillo et al., "The In Vitro Senescence of Human T Memory T Cell Phenotype," *Mech. Aging Develop.* 67:173–185 (1993)), confirming that proliferative senescence does not constitute a generalized decline of function. Comparing the expression of CD28 in T cell cultures which had completed varying percentages of their in vitro proliferative lifespan, it was found that senescence is accompanied by a dramatic reduction in CD28 expression (FIG. 4). This decrease is in marked contrast to the stable undiminished expression of all other T cell markers tested (CD2, CD3, CD29, CD11a, CD44, CD45RO) (N. L. Perillo et al. (1993), supra).

Thus, the specific loss of CD28 expression in cultures which have reached a stage of proliferative senescence suggests that the CD28 negative cells in the centenarians may be those cells which have undergone an increased number of cell divisions.

This study provides the first demonstration that both peripheral blood T lymphocytes of elderly individuals and cultures of senescent T cells show a decline in the percentage of cells expressing the CD28 molecule. This activation molecule provides a critical costimulatory signal following engagement of the T cell receptor. In the absence of the second signal, T cells presented with antigen may enter a state of anergy, characterized by the failure to activate the IL-2 gene in response to further antigenic stimulation (M. K. Jenkins et al. (1991), supra; D. R. DaSilva et al., "Clonal Anergy Is Induced In Vitro by T Cell Receptor Occupancy in the Absence of Proliferation," *J. Immunol.* 147:3261–3267 (1991)). The alternative consequence of this decreased IL-2 gene expression is a lack of proliferation, although anergic cells may be long-lived and capable of both cytolysis and secretion of some other cytokines. In certain cases, lack of costimulation may even lead to activation-induced apoptosis (Y. Liu & C. A. Janeway, "Interferon-g Plays a Critical Role in induced Cell Death of Effector T Cell: A Third Mechanism of Self-Tolerance," *J. Exp. Med.* 172:1735–1740 (1990)).

The in vitro experiments on the phenomenon of proliferative senescence provide a possible explanation for the in vivo age-associated decline in the proportion of T cells expressing CD28. The senescent cultures, which have completed approximately 23 population doublings, are characterized by an inability to proliferate following restimulation with antigen, exposure to anti-CD3 in combination with anti-CD28, or to increasing doses of IL-2. These are deficits which have been repeatedly shown for T cells from aged donors (M. L. Thoman & W. O. Weigle (1989), supra; R. A. Miller (1990), supra; B. A. Effros (1993), supra; A. Grossmann et al., "Reduced Proliferation on T Unrelated to Defects in Transmembrane Signaling which are Predominantly in the CD4+ Subset," *Exp. Cell Res.* 180:367–382 (1989)). In addition, the functional integrity of T-cells in the senescent cultures agrees with results of limiting dilution experiments measuring cytotoxic potential of individual T cells derived from aged mice (R. A. Miller, "Age-Associated Decline in Precursor Frequency for Different T Cell Reactions with Preservation of Helper of Cytotoxic Effect per Precursor Cell," *J. immunol.* 132:63–68 (1984)), and also confirms other reports that CD28 is not required for cytotoxicity (A. Azuma et al. (1993), supra).

These results suggest, therefore, that the CD28-negative cells in the peripheral blood of centenarians also have reached a state of proliferative senescence. A recent report demonstrated that immunological memory in human T lymphocytes resides in a cellular population with a more rapid rate of division (C. A. Michie et al. "Lifespan of Human Lymphocyte Subsets Defined by CD45 Isoforms," *Nature* 360:264–265 (1992)). Thus, with time, an increasing proportion of T cells may become stimulated repeatedly with environmental antigens and may be more likely to reach their proliferative limit, with the accompanying loss of CD28. The increased likelihood of having cells that have reached their proliferative limit coupled with decreased output of mature T cells from the thymus may account for altered phenotype and function of T cells from aged individuals.

It has been shown that the age-associated proliferative defect in human T lymphocytes is due entirely to reduced proliferation in the $CD8^+$ rather than the $CD4^+$ subset (A. Grossmann et al. (1989), supra). The data in FIG. 3, showing a correlation between a decrease in the CD4/CD8 ratio (i.e. a relative increase in the proportion of $CD8^+$ cells) and the reduced. percentage of $CD28^+$ T-cells, provides a possible explanation for the above findings. It suggests that the increased proportion of $CD8^+$ is associated with an increasing percentage of cells which cannot be activated via the CD28 costimulatory pathway.

Recently it was reported that a small but variable proportion of T-cells from younger normal donors are CD28-negative (A. Azuma et al. (1993), supra). Consistent with the results in this Example, these CD28-negative lymphocytes are predominantly $CD8^+$, and they do not proliferate in response to mitogenic signals. It was also shown that the T cells from cord blood had <1% CD28-negative cells, further reinforcing the conclusion from this Example that CD28-negative cells increase with age.

The demonstration of increased CD28-negative cells within the peripheral blood of centenarians suggests that other costimulatory molecules may also show modulation with age and proliferative lifespan. This, in fact, is likely to be the case, since in a CD28-negative transgenic mouse model, the decline in immune function was not as severe as that observed in normal aging (A. Shahinian et al., "Differential T Cell Costimulatory Requirements in CD28-Deficient Mice," *Science* 261:609–612 (1993)). In addition, in the transgenic mice, only some of the functions known to decline with age were affected. This mouse model, however, may not accurately reflect the age-associated CD28 decline demonstrated in centenarians and in prolonged in vitro cultures in this Example, because the aged T cells have presumably modulated their CD28 expression in response to certain other unspecified intracellular events.

In conclusion, the decline in the number of $CD28^+$ T cells with age provides a possible explanation for many of the previous findings on decreased proliferative response to mitogens, reduced delayed-type hypersensitivity response to recall antigens, and diminished antibody response to influenza vaccines in the elderly (B. A. Effros (1993), supra). It has been recently shown that in HIV+ individuals, there is a strong positive correlation between the lack of CD28 expression and poor mitogen-induced T cell proliferation. Although the results of this Example do not necessarily explain all types of age-associated changes in immune responsiveness which have been identified, e.g. in vitro stimulation with anti-CD3 and phorbol esters, a regimen which bypasses CD28, they are suggestive of at least one mechanism for changes in immune responsiveness. Nevertheless, if the CD28-negative subset were shown to be a predominant factor in proliferative decline, this would be consistent with the previous hypothesis that the age-associated decline in immune function is due to a decreased number of reactive cells rather than to a decline in the activity of all cells_(R. A. Miller (1990), supra).

In addition, because the study reported in this Example involved centenarians, who, by virtue of their longevity, presumably represent a high level of immunocompetence, it is predicted that studies on populations of ages 75–85 will reveal even more pronounced deficits in CD8 expression. In this regard, since the reduced T cell proliferative response of elderly individuals has been shown to be predictive of subsequent early mortality (D. M. Murasko et al. (1988), supra), an analysis of CD28 expression may provide a reliable biomarker for screening aged individuals for immunosenescence. The major challenge for future research in this area will be to define the mechanism responsible for CD28 down-regulation with age to determine if the relatively poor proliferative responses of CD28-negative lymphocytes can be reversed. In this regard, in vitro culture system reported in this Example provides an excellent experimental model for dissecting the cellular processes involved in modulating this key activation molecule.

ADVANTAGES OF THE INVENTION

The present invention provides an improved method of determining immune senescence in T cells. This improved method is broadly applicable. It does not be depend on markers or antigens that are found in only small subpopulations of immune-competent cells or whose occurrence varies markedly from individual to individual. This means that the results produced by the method are easy to interpret and are not subject to variability induced by other factors influencing immune response. The method is also relatively easy to carry out and interpret, while yielding results of predictive value, both for mortality and morbidity in general, and for susceptibility to particular immune-related conditions. The method is also be capable of combination with other screening methods for other markers so that a number of parameters of the cells can be determined in parallel. The method can also be used to separate and isolate immunologically senescent cells from immunologically non-senescent cells.

The method is particularly useful in diagnosing and determining the existence or likelihood of immune deficits in the elderly resulting from senescence of immune function. Accordingly, it can be used to determine patients who are most likely to be at risk immmunologically and to target these patients for more intensive study, prophylaxis, or attempts at immunostimulation or immunomodulation. The method can also be useful to study patients who, although not elderly, are likely to become immunocompromised, such as Down's Syndrome patients, or patients infected with HIV.

Although the present invention has been described in considerable detail with regard to certain preferred versions thereof, other versions are possible. Therefore, the spirit and scope of the appended claims should not be limited to the descriptions of the preferred versions contained herein.

I claim:

1. A method to identify replicatively senescent T-cells in a sample containing T-cells comprising:

determining the presence or absence of CD28 and CD3 on a surface of the cells of said sample; and identifying replicatively senescent T-cells as possessing CD3 ($CD3^+$) and lacking CD28 ($CD28^-$); wherein replicatively senescent T-cells are characterized as being unable to undergo cell division and wherein a first monoclonal antibody that binds to CD3 and a second monoclonal antibody that binds to CD28 are used to identify the presence or absence of CD3 and CD28 on the surface of said cells.

2. The method of claim 1, wherein said samples isolated peripheral blood mononuclear cells.

3. The method of claim 1 wherein said first and said second monoclonal antibodies we detectably labeled and flow cytometric analysis is used to identify cells that bind said first or said second antibodies, or both.

4. The method of claim 2 wherein said first and said second monoclonal antibodies are detectably labeled and flow cytometric analysis is used to identify cells that bind said first or said second antibodies, or both.

5. The method of claim 1 further comprising: determining the presence of CD8 on the surface of said cells, wherein the presence of CD3 and CD8, $CD3^+CD8^+$, and the absence of CD28, $CD28^-$, on a cell identifies a replicatively senescent T-cell that is a replicatively senescent cytotoxic T-cell.

6. The method of claim 2 further comprising: determining the presence of CD8 on the surface of said cells, wherein the presence of CD3 and CD8, $CD3^+CD8^+$, and the absence of CD28, $CD28^-$, on a cell identifies a replicatively senescent T-cell that is a replicatively senescent cytotoxic T-cell.

7. The method of claim 2 wherein a percentage of replicatively senescent T-cells is determined as the percentage of $CD3^+$ cells that are $CD28^-$ in said sample.

8. The method of claim 5 wherein a percentage of replicatively senescent cytotoxic T-cells is determined as the percentage of $CD3^+CD8^+$ cells that are $CD28^-$ in said sample.

9. The method of claim 6 wherein a percentage of replicatively senescent cytotoxic T-cells is determined as the percentage of $CD3^+CD8^+$ cells that are $CD28^-$ in said sample.

10. The method of claim 7, wherein said method is used to identify samples from individuals with reduced T-cell responsiveness and wherein reduced T-cell responsiveness is characterized by a higher percentage of $CD3^+$ cells that are $CD28^-$ when compared to a sample from an immunocompetent individual.

11. The method of claim 8, wherein said method is used to identify samples from individuals with reduced T-cell responsiveness and wherein reduced T-cell responsiveness is characterized by a higher percentage of $CD3^+$ cells that are $CD28^-$ when compared to a sample from an immunocompetent individual.

12. The method of claim 10 wherein an individual with a reduced T-cell responsiveness is characterized by having 50% or more $CD28^-CD3^+$ cells.

13. The method of claim 11 wherein an individual with a reduced T-cell responsiveness is characterized by having 50% or more $CD28^-CD3^+$ cells.

* * * * *